United States Patent
Thompson et al.

(10) Patent No.: US 12,059,228 B2
(45) Date of Patent: *Aug. 13, 2024

(54) CONNECTION SYSTEMS AND METHODS FOR ESTABLISHING OPTICAL AND ELECTRICAL CONNECTIONS THROUGH A DRAPE

(71) Applicant: Bard Access Systems, Inc., Salt Lake City, UT (US)

(72) Inventors: Chase Thompson, Bountiful, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/235,334

(22) Filed: Aug. 17, 2023

(65) Prior Publication Data

US 2023/0390015 A1 Dec. 7, 2023

Related U.S. Application Data

(63) Continuation of application No. 16/923,912, filed on Jul. 8, 2020, now Pat. No. 11,737,848.

(Continued)

(51) Int. Cl.
*A61B 46/10* (2016.01)
*A61B 5/00* (2006.01)
*A61B 46/23* (2016.01)

(52) U.S. Cl.
CPC ............ *A61B 46/23* (2016.02); *A61B 5/0084* (2013.01); *A61B 5/6852* (2013.01); *A61B 2046/234* (2016.02)

(58) Field of Classification Search
CPC ... A61B 46/23; A61B 2046/234; A61B 39/18; A61B 1/00124; A61B 1/00142;
(Continued)

(56) References Cited

U.S. PATENT DOCUMENTS 2,831,174 A  4/1958 Hilmo
2,959,766 A  11/1960 Jacobsen
(Continued)

FOREIGN PATENT DOCUMENTS

EP   1318576 A1   6/2003
EP   3270817 A1   1/2018
(Continued)

OTHER PUBLICATIONS

"Sampling Accessories" Spectrometers Accessories Catalogue, pp. 71-102, XP055014465, retrieved from the Internet URL: http//www.mikropack.de/d/specto/pdfý-downoads/sampling accessories. pdf, Jan. 1, 2004 (Jan. 1, 2004).
(Continued)

*Primary Examiner* — Camtu T Nguyen
(74) *Attorney, Agent, or Firm* — Rutan & Tucker LLP (57) ABSTRACT

Connection systems and methods for establishing optical and electrical connections through a drape are disclosed. A connection system can include a plug and a receptacle, the plug being configured to insert into the receptacle with the drape therebetween. The plug can include an optical terminal extending from a plug housing and an electrical terminal extending from the plug housing. The electrical terminal can be configured as a piercing element for piercing the drape. The receptacle can include an optical receiver within a receptacle housing and an electrical receiver within the receptacle housing. The optical receiver can be configured to form the optical connection with the optical terminal, and the electrical receiver can be configured to form the elec-
(Continued)

trical connection with the electrical terminal when the plug is inserted into the receptacle with the drape therebetween.

9 Claims, 10 Drawing Sheets

Related U.S. Application Data (60) Provisional application No. 62/879,966, filed on Jul. 29, 2019.

(58) Field of Classification Search
CPC ..... A61B 5/062; A61B 5/6852; A61B 5/0245; A61B 5/24; A61B 2034/2051
See application file for complete search history.

(56) References Cited

U.S. PATENT DOCUMENTS

| | | |
|---|---|---|
| 3,329,928 A | 7/1967 | Broske |
| 3,532,095 A | 10/1970 | Miller et al. |
| 3,597,582 A | 8/1971 | Goode et al. |
| 3,605,743 A | 9/1971 | Arce |
| 3,649,952 A | 3/1972 | Harmon |
| 3,665,372 A | 5/1972 | Goode et al. |
| 3,673,548 A | 6/1972 | Mattingly, Jr. et al. |
| 3,746,814 A | 7/1973 | Lackey et al. |
| 3,824,556 A | 7/1974 | Berkovits et al. |
| 3,842,394 A | 10/1974 | Bolduc |
| 4,200,348 A | 4/1980 | Stupay |
| 4,220,387 A | 9/1980 | Biche et al. |
| 4,254,764 A | 3/1981 | Neward |
| 4,303,293 A | 12/1981 | Grunwald |
| 4,369,794 A | 1/1983 | Furler |
| 4,490,003 A | 12/1984 | Robinson |
| 4,614,395 A | 9/1986 | Peers-Trevarton |
| 4,632,121 A | 12/1986 | Johnson et al. |
| 4,700,997 A | 10/1987 | Strand |
| 4,702,256 A | 10/1987 | Robinson et al. |
| 4,761,143 A | 8/1988 | Owens et al. |
| 4,858,810 A | 8/1989 | Intlekofer et al. |
| 4,860,742 A | 8/1989 | Park et al. |
| 4,973,329 A | 11/1990 | Park et al. |
| 5,159,861 A | 11/1992 | Anderson |
| 5,178,159 A | 1/1993 | Christian |
| 5,217,435 A | 6/1993 | Kring |
| 5,325,746 A | 7/1994 | Anderson |
| 5,325,868 A | 7/1994 | Kimmelstiel |
| 5,334,045 A | 8/1994 | Cappa et al. |
| 5,354,326 A | 10/1994 | Comben et al. |
| 5,407,368 A | 4/1995 | Strand et al. |
| 5,423,877 A | 6/1995 | Mackey |
| 5,437,277 A | 8/1995 | Dumoulin et al. |
| 5,454,739 A | 10/1995 | Strand |
| 5,482,038 A | 1/1996 | Ruff |
| 5,489,225 A | 2/1996 | Julian |
| 5,501,675 A | 3/1996 | Erskine |
| 5,538,444 A | 7/1996 | Strand et al. |
| 5,560,358 A | 10/1996 | Arnold et al. |
| 5,591,119 A | 1/1997 | Adair |
| 5,624,281 A | 4/1997 | Christensson |
| 5,685,855 A | 11/1997 | Erskine |
| 5,752,915 A | 5/1998 | Neubauer et al. |
| 5,766,042 A | 6/1998 | Ries et al. |
| 5,769,786 A | 6/1998 | Wiegel |
| 5,797,880 A | 8/1998 | Erskine |
| 5,840,024 A | 11/1998 | Taniguchi et al. |
| 5,968,082 A | 10/1999 | Heil |
| 5,984,918 A | 11/1999 | Garito et al. |
| 6,050,976 A | 4/2000 | Thorne et al. |
| 6,090,052 A | 7/2000 | Akerfeldt et al. |
| 6,102,044 A | 8/2000 | Naidyhorski |
| 6,132,368 A | 10/2000 | Cooper |
| 6,140,722 A | 10/2000 | Ballard et al. |
| 6,162,101 A | 12/2000 | Fischer et al. |
| 6,319,015 B1 | 11/2001 | Faunce |
| 6,324,416 B1 | 11/2001 | Seibert |
| 6,330,480 B1 | 12/2001 | Van der Linden et al. |
| 6,350,160 B1 | 2/2002 | Feuersanger et al. |
| 6,415,168 B1 | 7/2002 | Putz |
| 6,428,336 B1 | 8/2002 | Akerfeldt |
| 6,546,270 B1 | 4/2003 | Goldin et al. |
| 6,620,136 B1 | 9/2003 | Pressly, Sr. et al. |
| 6,663,570 B2 | 12/2003 | Mott et al. |
| 6,673,078 B1 | 1/2004 | Muncie |
| 6,714,809 B2 | 3/2004 | Lee et al. |
| 6,780,065 B2 | 8/2004 | Schwarz |
| 6,799,991 B2 | 10/2004 | Williams et al. |
| 6,913,478 B2 | 7/2005 | Lamirey |
| 7,130,699 B2 | 10/2006 | Huff et al. |
| 7,144,378 B2 | 12/2006 | Arnott |
| 7,255,609 B1 | 8/2007 | Epstein |
| 7,274,956 B2 | 9/2007 | Mott et al. |
| 7,402,083 B2 | 7/2008 | Kast et al. |
| 7,452,360 B2 | 11/2008 | Trudeau et al. |
| 7,553,193 B2 | 6/2009 | Kast et al. |
| 7,585,118 B1 | 9/2009 | Lumpkin |
| 7,633,023 B1 | 12/2009 | Cappa et al. |
| 7,666,191 B2 | 2/2010 | Orban, III et al. |
| 7,753,696 B2 | 7/2010 | Hoecke et al. |
| 7,771,394 B2 | 8/2010 | Shue et al. |
| 7,819,844 B2 | 10/2010 | Spenser et al. |
| 7,972,282 B2 | 7/2011 | Clark et al. |
| 8,105,338 B2 | 1/2012 | Anderson et al. |
| 8,147,275 B1 | 4/2012 | Drake et al. |
| 8,206,175 B2 | 6/2012 | Boyd et al. |
| 8,267,873 B2 | 9/2012 | Yanuma |
| 8,388,541 B2 | 3/2013 | Messerly et al. |
| 8,480,427 B2 | 7/2013 | Marshalok |
| 8,548,601 B2 | 10/2013 | Chinn et al. |
| 8,597,042 B2 | 12/2013 | King |
| 8,603,011 B2 | 12/2013 | Landowski |
| 8,620,412 B2 | 12/2013 | Griffiths et al. |
| 8,639,340 B2 | 1/2014 | Sommer et al. |
| 8,666,510 B2 | 3/2014 | Chinn et al. |
| 8,781,555 B2 | 7/2014 | Burnside et al. |
| 8,849,382 B2 | 9/2014 | Cox et al. |
| 8,869,887 B2 | 10/2014 | Deere et al. |
| 8,932,258 B2 | 1/2015 | Blanchard et al. |
| 8,958,878 B2 | 2/2015 | Cejnar |
| 9,059,548 B2 | 6/2015 | Stump et al. |
| 9,095,680 B2 | 8/2015 | Steegers et al. |
| 9,101,775 B2 | 8/2015 | Barker |
| 9,107,594 B2 | 8/2015 | Selvitelli et al. |
| 9,108,027 B2 | 8/2015 | Eubanks et al. |
| 9,131,956 B2 | 9/2015 | Shaughnessy et al. |
| 9,144,395 B2 | 9/2015 | Sela et al. |
| 9,425,537 B2 | 8/2016 | Barker |
| 9,456,766 B2 | 10/2016 | Cox et al. |
| 9,492,097 B2 | 11/2016 | Wilkes et al. |
| 9,521,961 B2 | 12/2016 | Silverstein et al. |
| 9,526,440 B2 | 12/2016 | Burnside et al. |
| 9,549,685 B2 | 1/2017 | Cox et al. |
| 9,554,716 B2 | 1/2017 | Burnside et al. |
| 9,636,031 B2 | 5/2017 | Cox |
| 9,649,048 B2 | 5/2017 | Cox et al. |
| 9,656,093 B2 | 5/2017 | Villarta et al. |
| 9,662,506 B2 | 5/2017 | Govea |
| 9,675,784 B2 | 6/2017 | Belson |
| 9,681,823 B2 | 6/2017 | Messerly et al. |
| 9,808,647 B2 | 11/2017 | Rhodes et al. |
| 9,872,971 B2 | 1/2018 | Blanchard |
| 9,919,145 B2 | 3/2018 | Bondhus et al. |
| 9,950,139 B2 | 4/2018 | Blanchard et al. |
| 9,999,371 B2 | 6/2018 | Messerly et al. |
| 10,105,121 B2 | 10/2018 | Burnside et al. |
| 10,130,806 B2 | 11/2018 | Leven et al. |
| 10,165,962 B2 | 1/2019 | Messerly et al. |
| 10,201,713 B2 | 2/2019 | Leven |
| 10,231,753 B2 | 3/2019 | Burnside et al. |
| 10,238,418 B2 | 3/2019 | Cox et al. |
| 10,238,880 B2 | 3/2019 | Thom et al. |
| 10,307,602 B2 | 6/2019 | Leven |
| 10,322,253 B2 | 6/2019 | Einav et al. |

(56) References Cited

U.S. PATENT DOCUMENTS

| | | |
|---|---|---|
| 10,342,575 B2 | 7/2019 | Cox et al. |
| 10,449,330 B2 | 10/2019 | Newman et al. |
| 10,524,691 B2 | 1/2020 | Newman et al. |
| 10,602,958 B2 | 3/2020 | Silverstein et al. |
| 10,751,509 B2 | 8/2020 | Misener |
| 10,772,696 B2 | 9/2020 | Thompson et al. |
| 10,992,078 B2 | 4/2021 | Thompson et al. |
| D921,884 S | 6/2021 | Tran et al. |
| 2002/0197905 A1 | 12/2002 | Kaufmann et al. |
| 2003/0199827 A1 | 10/2003 | Thorne |
| 2003/0216723 A1 | 11/2003 | Shinmura et al. |
| 2004/0039372 A1 | 2/2004 | Carmody |
| 2004/0146252 A1 | 7/2004 | Healy et al. |
| 2005/0177199 A1 | 8/2005 | Hansen et al. |
| 2005/0283216 A1 | 12/2005 | Pyles |
| 2006/0025677 A1 | 2/2006 | Verard et al. |
| 2006/0030864 A1 | 2/2006 | Kennedy et al. |
| 2006/0161138 A1 | 7/2006 | Orban et al. |
| 2006/0173407 A1 | 8/2006 | Shaughnessy et al. |
| 2007/0062544 A1 | 3/2007 | Rauk Bergstrom et al. |
| 2007/0118079 A1 | 5/2007 | Moberg et al. |
| 2007/0160327 A1 | 7/2007 | Ewallen et al. |
| 2007/0161969 A1 | 7/2007 | Andersen |
| 2007/0293719 A1 | 12/2007 | Scopton et al. |
| 2008/0009720 A1 | 1/2008 | Schefelker et al. |
| 2008/0046062 A1 | 2/2008 | Camps et al. |
| 2008/0236598 A1 | 10/2008 | Gobel |
| 2008/0287876 A1 | 11/2008 | Shue et al. |
| 2008/0304793 A1 | 12/2008 | Benaron et al. |
| 2009/0156926 A1 | 6/2009 | Messerly et al. |
| 2009/0234328 A1 | 9/2009 | Cox et al. |
| 2010/0036227 A1 | 2/2010 | Cox et al. |
| 2010/0049126 A1* | 2/2010 | Bronfeld .......... A61B 5/150114 604/113 |
| 2010/0139669 A1 | 6/2010 | Piferi et al. |
| 2010/0204569 A1 | 8/2010 | Burnside et al. |
| 2011/0015533 A1 | 1/2011 | Cox et al. |
| 2011/0160824 A1 | 6/2011 | Ware et al. |
| 2011/0166528 A1 | 7/2011 | Millerd et al. |
| 2011/0250775 A1 | 10/2011 | Bies et al. |
| 2011/0257503 A1 | 10/2011 | Mehdizadeh et al. |
| 2011/0282188 A1 | 11/2011 | Burnside et al. |
| 2011/0295108 A1 | 12/2011 | Cox et al. |
| 2012/0071752 A1 | 3/2012 | Sewell et al. |
| 2012/0143029 A1 | 6/2012 | Silverstein et al. |
| 2012/0220854 A1 | 8/2012 | Messerly et al. |
| 2012/0253320 A1 | 10/2012 | Steegers et al. |
| 2013/0006102 A1 | 1/2013 | Wilkes et al. |
| 2013/0023729 A1 | 1/2013 | Vazales et al. |
| 2013/0060116 A1 | 3/2013 | Messerly et al. |
| 2013/0095689 A1 | 4/2013 | Hayman et al. |
| 2013/0104884 A1 | 5/2013 | Vazales et al. |
| 2013/0109980 A1 | 5/2013 | Teo |
| 2013/0211225 A1 | 8/2013 | Zhang |
| 2013/0245434 A1 | 9/2013 | Messerly et al. |
| 2013/0247921 A1* | 9/2013 | Dye ...................... A61B 90/40 128/853 |
| 2013/0289417 A1 | 10/2013 | Grunwald et al. |
| 2013/0308137 A1 | 11/2013 | Manzke et al. |
| 2013/0331688 A1 | 12/2013 | Heigl et al. |
| 2013/0337674 A1 | 12/2013 | Stump et al. |
| 2014/0031674 A1 | 1/2014 | Newman et al. |
| 2014/0046261 A1 | 2/2014 | Newman et al. |
| 2014/0107475 A1 | 4/2014 | Cox et al. |
| 2014/0150782 A1 | 6/2014 | Vazales et al. |
| 2014/0188133 A1 | 7/2014 | Misener |
| 2014/0303492 A1 | 10/2014 | Burnside et al. |
| 2015/0012072 A1 | 1/2015 | Johnson et al. |
| 2015/0018701 A1 | 1/2015 | Cox et al. |
| 2015/0031987 A1 | 1/2015 | Pameijer et al. |
| 2015/0105654 A1 | 4/2015 | Meyer |
| 2015/0148615 A1 | 5/2015 | Brennan et al. |
| 2015/0164583 A1 | 6/2015 | Zarins et al. |
| 2015/0177467 A1 | 6/2015 | Gniadek et al. |
| 2015/0190615 A1 | 7/2015 | Shaltis |
| 2015/0223897 A1 | 8/2015 | Kostrzewski et al. |
| 2015/0297114 A1 | 10/2015 | Cox et al. |
| 2015/0305816 A1 | 10/2015 | Hadzic |
| 2016/0018602 A1* | 1/2016 | Govari .................. G02B 6/3826 385/71 |
| 2016/0213432 A1 | 7/2016 | Flexman et al. |
| 2017/0014194 A1 | 1/2017 | Duindam et al. |
| 2017/0020561 A1 | 1/2017 | Cox et al. |
| 2017/0079548 A1 | 3/2017 | Silverstein et al. |
| 2017/0079615 A1 | 3/2017 | Burnside et al. |
| 2017/0079681 A1 | 3/2017 | Burnside et al. |
| 2017/0231700 A1 | 8/2017 | Cox et al. |
| 2017/0261699 A1* | 9/2017 | Compton ............. G02B 6/3821 |
| 2017/0281029 A1 | 10/2017 | Messerly et al. |
| 2017/0333136 A1 | 11/2017 | Hladio et al. |
| 2018/0071509 A1 | 3/2018 | Tran et al. |
| 2018/0110951 A2 | 4/2018 | Beard |
| 2018/0116551 A1 | 5/2018 | Newman et al. |
| 2018/0140170 A1 | 5/2018 | Van Putten et al. |
| 2018/0289927 A1 | 10/2018 | Messerly |
| 2018/0296122 A1 | 10/2018 | Messerly et al. |
| 2019/0069877 A1* | 3/2019 | Burnside ................ A61B 90/40 |
| 2019/0099108 A1 | 4/2019 | Messerly et al. |
| 2019/0231172 A1* | 8/2019 | Barron ............... A61B 1/00124 |
| 2019/0237902 A1 | 8/2019 | Thompson et al. |
| 2019/0350621 A1 | 11/2019 | Zitnick et al. |
| 2019/0350663 A1 | 11/2019 | Thompson et al. |
| 2020/0054858 A1 | 2/2020 | Newman et al. |
| 2020/0138332 A1 | 5/2020 | Newman et al. |
| 2020/0221934 A1 | 7/2020 | Van Der Mark et al. |
| 2020/0237255 A1 | 7/2020 | Silverstein et al. |
| 2020/0345441 A1* | 11/2020 | Thompson ............. A61B 46/23 |
| 2021/0030504 A1 | 2/2021 | Thompson et al. |
| 2021/0038322 A1 | 2/2021 | Thompson et al. |
| 2022/0110707 A1 | 4/2022 | Sowards et al. |
| 2022/0110708 A1 | 4/2022 | Misener et al. |
| 2022/0128770 A1 | 4/2022 | Sowards et al. |
| 2022/0241044 A1 | 8/2022 | Thompson et al. |
| 2023/0248459 A1 | 8/2023 | Thompson et al. |

FOREIGN PATENT DOCUMENTS

| | | |
|---|---|---|
| EP | 3673801 A1 | 7/2020 |
| WO | 9413201 A1 | 6/1994 |
| WO | 9619017 A1 | 6/1996 |
| WO | 9822180 A1 | 5/1998 |
| WO | 2004101068 A1 | 11/2004 |
| WO | 2005016451 A1 | 2/2005 |
| WO | 2005044332 A2 | 5/2005 |
| WO | 2005072807 A1 | 8/2005 |
| WO | 2005077453 A2 | 8/2005 |
| WO | 2007058816 A2 | 5/2007 |
| WO | 2007109285 A2 | 9/2007 |
| WO | 2007149618 A2 | 12/2007 |
| WO | 2009050599 A2 | 4/2009 |
| WO | 2010123701 A1 | 10/2010 |
| WO | 2011033107 A1 | 3/2011 |
| WO | 2011082160 A2 | 7/2011 |
| WO | 2012102745 A2 | 8/2012 |
| WO | 2015075002 A1 | 5/2015 |
| WO | 2016146993 A1 | 9/2016 |
| WO | 2019148201 A1 | 8/2019 |
| WO | 2019165011 A1 | 8/2019 |
| WO | 2019191926 A1 | 11/2019 |
| WO | 2021021408 A1 | 2/2021 |
| WO | 2021026502 A1 | 2/2021 |
| WO | 2022081583 A1 | 4/2022 |
| WO | 2022081591 A1 | 4/2022 |
| WO | 2022093991 A1 | 5/2022 |

OTHER PUBLICATIONS

EP 20849119.1 filed Mar. 4, 2022 Extended European Search Report dated Jun. 26, 2023.
PCT/US19/30470 filed May 2, 2019 International Search Report and Written Opinion dated Jul. 19, 2019.
PCT/US2019/015710 filed Jan. 29, 2019 International Preliminary Report on Patentability dated Apr. 29, 2019.

(56) References Cited

OTHER PUBLICATIONS

PCT/US2019/015710 filed Jan. 29, 2019 International Search Report and Written Opinion dated Apr. 29, 2019.
PCT/US2019/018851 filed Feb. 20, 2019 Internation Search Report and Written Opinion dated May 7, 2019.
PCT/US2019/018851 filed Feb. 20, 2019 International Preliminary Report on Patentability dated May 7, 2019.
PCT/US2020/41267 filed Jul. 8, 2020 Internation Search Report and Written Opinion dated Oct. 1, 2020.
PCT/US2020/45498 filed Aug. 7, 2020 International Search Report and Written Opinion dated Oct. 4, 2020.
PCT/US2021/054593 filed Oct. 12, 2021 International Search Report and Written Opinion dated Jan. 24, 2022.
PCT/US2021/054607 filed Oct. 12, 2021 International Search Report and Written Opinion dated Jan. 21, 2022.
PCT/US2021/056896 filed Oct. 27, 2021 International Search Report and Written Opinion dated Mar. 22, 2022.
U.S. Appl. No. 12/426,175 filed Apr. 17, 2009 Advisory Action dated Nov. 26, 2013.
U.S. Appl. No. 12/426,175 filed Apr. 17, 2009 Decision on Appeal dated Nov. 7, 2016.
U.S. Appl. No. 12/426,175 filed Apr. 17, 2009 Examiner's Answer dated Oct. 7, 2014.
U.S. Appl. No. 12/426,175 filed Apr. 17, 2009 Final Office Action dated Aug. 2, 2013.
U.S. Appl. No. 12/426,175 filed Apr. 17, 2009 Final Office Action dated Jan. 31, 2014.
U.S. Appl. No. 12/426,175 filed Apr. 17, 2009 Non-Final Office Action dated Dec. 3, 2012.
U.S. Appl. No. 12/426,175 filed Apr. 17, 2009 Notice of Allowance dated Dec. 13, 2016.
U.S. Appl. No. 12/715,556, filed Mar. 2, 2010 Final Office Action dated Oct. 2, 2013.
U.S. Appl. No. 12/715,556, filed Mar. 2, 2010 Non-Final Office Action dated Sep. 13, 2012.
U.S. Appl. No. 15/585,051, filed May 2, 2017 Examiner's Answer dated May 2, 2019.
U.S. Appl. No. 15/585,051, filed May 2, 2017 Final Office Action dated Feb. 28, 2018.
U.S. Appl. No. 15/585,051, filed May 2, 2017 Final Office Action dated Mar. 15, 2018.
U.S. Appl. No. 15/585,051, filed May 2, 2017 Non-Final Office Action dated Jul. 14, 2017.
U.S. Appl. No. 16/261,368, filed Jan. 29, 2019 Advisory Action dated Jul. 21, 2020.
U.S. Appl. No. 16/261,368, filed Jan. 29, 2019 Non-Final Office Action dated Jan. 23, 2020.
U.S. Appl. No. 16/261,368, filed Jan. 29, 2019 Notice of Allowance dated Jan. 15, 2021.
U.S. Appl. No. 16/281,079, filed Feb. 20, 2019 Board Decision dated Jun. 6, 2023.
U.S. Appl. No. 16/281,079, filed Feb. 20, 2019 Examiner's Answer dated Feb. 25, 2022.
U.S. Appl. No. 16/281,079, filed Feb. 20, 2019 Final Office Action dated Aug. 25, 2020.
U.S. Appl. No. 16/281,079, filed Feb. 20, 2019 Non-Final Office Action dated Apr. 1, 2020.
U.S. Appl. No. 16/281,079, filed Feb. 20, 2019 Non-Final Office Action dated Apr. 20, 2021.
U.S. Appl. No. 16/402,074, filed May 2, 2019 Non-Final Office Action dated Apr. 16, 2020.
U.S. Appl. No. 16/923,912, filed Jul. 8, 2020 Notice of Allowance dated Mar. 27, 2023.
U.S. Appl. No. 16/932,425, filed Jul. 17, 2020 Non-Final Office Action dated Jun. 18, 2021.
U.S. Appl. No. 16/932,425, filed Jul. 17, 2020 Notice of Allowance dated Jan. 10, 2022.
U.S. Appl. No. 16/988,452, filed Aug. 7, 2020 Final Office Action dated Mar. 16, 2023.
U.S. Appl. No. 16/988,452, filed Aug. 7, 2020 Non-Final Office Action dated Mar. 16, 2023.
U.S. Appl. No. 17/240,826, filed Apr. 26, 2021, Non-Final Office Action dated Jul. 19, 2023.
U.S. Appl. No. 17/512,501, filed Oct. 27, 2021 Non-Final Office Action dated Feb. 17, 2023.
U.S. Appl. No. 17/512,501, filed Oct. 27, 2021 Restriction Requirement dated Sep. 30, 2022.
U.S. Appl. No. 17/723,246, filed Apr. 18, 2022, Non-Final Office Action dated Sep. 27, 2022.
U.S. Appl. No. 17/723,246, filed Apr. 18, 2022, Notice of Allowance dated Jan. 27, 2023.
Design U.S. Appl. No. 29/658,136 Specification and Drawings filed Jul. 27, 2018.

\* cited by examiner

CONNECTION SYSTEMS AND METHODS FOR ESTABLISHING OPTICAL AND ELECTRICAL CONNECTIONS THROUGH A DRAPE

PRIORITY

This application is a continuation of U.S. patent application Ser. No. 16/923,912, filed Jul. 8, 2020, now U.S. Pat. No. 11,737,848, which claims the benefit of priority to U.S. Provisional Application No. 62/879,966, filed Jul. 29, 2019, each of which is incorporated by reference in its entirety into this application.

BACKGROUND

At times, a tip of a peripherally inserted central catheter ("PICC") or central venous catheter ("CVC") can move, becoming displaced from an ideal position in a patient's superior vena cava ("SVC"). A clinician believing such a PICC or CVC has displaced typically checks for displacement by chest X-ray and replaces the PICC or CVC if necessary. Because X-rays expose patients to ionizing radiation, medical devices such as PICCs and CVCs are being developed with integrated optical-fiber stylets for clinicians to easily and safely check for displacement thereof by way of shape sensing with the optical-fiber stylets. However, in order for the clinicians to check for displacement, the PICCs or CVCs, which are sterile as provided, need to be optically and electrically connected to non-sterile capital equipment without compromising sterile conditions. Therefore, there is a need for a connection system that allows for single-use medical devices such as the foregoing PICCs and CVCs to be optically and electrically connected to non-sterile capital equipment without compromising sterile conditions.

Disclosed herein are connection systems and methods thereof that address at least the foregoing need.

SUMMARY

Disclosed herein is a connection system for establishing both an optical connection and an electrical connection through a drape. The connection system includes, in some embodiments, a plug and a receptacle, wherein the plug is configured to insert into the receptacle with the drape therebetween. The plug includes a plug housing, an optical terminal extending from the plug housing, and an electrical terminal extending from the plug housing. The electrical terminal is configured as a piercing element for piercing the drape. The receptacle includes a receptacle housing, an optical receiver within the receptacle housing, and an electrical receiver within the receptacle housing. The optical receiver is configured to form the optical connection with the optical terminal when the plug is inserted into the receptacle with the drape therebetween. The electrical receiver is configured to form the electrical connection with the electrical terminal when the plug is inserted into the receptacle with the drape therebetween.

In some embodiments, the piercing element includes a longitudinal cutout between the plug housing and a tip of the piercing element. The optical terminal extends from the plug housing into the longitudinal cutout of the piercing element.

In some embodiments, the piercing element is configured to deflect away from a longitudinal axis of the plug to expose the optical terminal.

In some embodiments, the electrical receiver includes a channel configured to deflect the piercing element away from the longitudinal axis of the plug upon inserting the plug into the receptacle. Deflecting the piercing element away from the longitudinal axis of the plug exposes the optical terminal for insertion into the optical receiver and formation of the optical connection.

In some embodiments, the channel of the electrical receiver is configured to keep the piercing element deflected away from the longitudinal axis of the plug. The channel of the electrical receiver is also configured form the electrical connection with an electrical contact within the electrical receiver upon fully inserting the plug into the receptacle.

In some embodiments, the piercing element is configured to deflect toward a longitudinal side of the plug.

In some embodiments, the electrical receiver includes a channel configured to deflect the piercing element toward the longitudinal side of the plug upon inserting the plug into the receptacle. Deflect the piercing element toward the longitudinal side of the plug exposes the optical terminal for insertion into the optical receiver and formation of the optical connection.

In some embodiments, the channel of the electrical receiver is configured to keep the piercing element deflected toward the longitudinal side of the plug. The channel of the electrical receiver is also configured to form the electrical connection with an electrical contact within the electrical receiver upon fully inserting the plug into the receptacle.

In some embodiments, the optical terminal includes an optical fiber extending from the plug housing into a ferrule, and the optical receiver includes an optical fiber disposed in a ferrule at a closed end of the optical receiver.

In some embodiments, the ferrules connect in a straight sleeve-type butt-joint connection.

In some embodiments, the ferrules connect in a tapered sleeve-type butt-joint connection.

In some embodiments, the plug is configured to simultaneously make both the optical and electrical connections with the receptacle from a sterile field established by the drape without compromising sterility of the sterile field.

Also disclosed herein is a connection system for establishing both an optical connection and an electrical connection through a drape. The connection system includes, in some embodiments, a plug and a receptacle, wherein the plug is configured to insert into the receptacle with the drape therebetween. The plug includes a plug housing, an optical terminal extending from the plug housing, and an electrical terminal extending from the plug housing. The optical terminal includes an optical fiber extending from the plug housing into a ferrule. The electrical terminal is configured as a piercing element for piercing the drape. The piercing element includes a longitudinal cutout between the plug housing and a tip of the piercing element, and the optical terminal extends from the plug housing into the longitudinal cutout of the piercing element. The receptacle includes a receptacle housing, an optical receiver within the receptacle housing, and an electrical receiver within the receptacle housing. The optical receiver is configured to form the optical connection with the optical terminal when the plug is inserted into the receptacle with the drape therebetween. The optical receiver including an optical fiber disposed in a ferrule at a closed end of the optical receiver. The electrical receiver is configured to form the electrical connection with the electrical terminal when the plug is inserted into the receptacle with the drape therebetween.

In some embodiments, the electrical receiver includes a channel configured to deflect the piercing element away from a longitudinal axis of the plug or toward a longitudinal side of the plug upon inserting the plug into the receptacle.

Deflecting the piercing element away from the longitudinal axis of the plug or toward the longitudinal side of the plug exposes the optical terminal for insertion into the optical receiver and formation of the optical connection.

In some embodiments, the channel of the electrical receiver is configured to keep the piercing element deflected away from the longitudinal axis or toward the longitudinal side of the plug. The channel of the electrical receiver is also configured form the electrical connection with an electrical contact within the electrical receiver upon fully inserting the plug into the receptacle.

In some embodiments, the plug is configured to simultaneously make both the optical and electrical connections with the receptacle from a sterile field established by the drape without compromising sterility of the sterile field.

Also disclosed herein is a method for establishing both an optical connection and an electrical connection through a drape including, in some embodiments, establishing a sterile field with the drape; piercing the drape from a sterile side thereof with an electrical terminal configured as a piercing element that extends from a plug, wherein the piercing element includes a longitudinal cutout between a housing of the plug and a tip of the piercing element in which cutout an optical terminal that extends from the plug is disposed; inserting the plug into a receptacle on a non-sterile side of the drape, wherein the receptacle includes an optical receiver and an electrical receiver within a receptacle housing configured to form the optical connection with the optical terminal and the electrical connection with the piercing element, respectively; and establishing both the optical and electrical connections through the drape without compromising sterility of the sterile field.

In some embodiments, piercing the drape with the piercing element simultaneously advances the optical terminal through the drape in accordance with disposition of the optical terminal in the cutout of the piercing element.

In some embodiments, inserting the plug into the receptacle includes inserting the piercing element into a channel of the electrical receiver. The channel is configured to deflect the piercing element away from a longitudinal axis of the plug or toward a longitudinal side of the plug. Deflecting the piercing element away from the longitudinal axis of the plug or toward the longitudinal side of the plug exposes the optical terminal.

In some embodiments, inserting the plug into the receptacle includes forming a butt-joint connection between a ferrule-covered portion of the optical terminal and a ferrule-covered portion of optical fiber at a closed end of the optical receiver.

These and other features of the concepts provided herein will become more apparent to those of skill in the art in view of the accompanying drawings and following description, which describe particular embodiments of such concepts in greater detail.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter.

That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

As set forth above, there is a need for a connection system that allows for single-use medical devices such as PICCs and CVCs to be optically and electrically connected to non-sterile capital equipment without compromising sterile conditions. Disclosed herein are connection systems and methods thereof that address at least the foregoing need.

For example, a connection system for establishing both an optical connection and an electrical connection through a drape is disclosed herein. The connection system includes, in some embodiments, a plug and a receptacle, wherein the plug is configured to insert into the receptacle with the drape therebetween. The plug includes a plug housing, an optical terminal extending from the plug housing, and an electrical terminal extending from the plug housing. The electrical terminal is configured as a piercing element for piercing the drape. The receptacle includes a receptacle housing, an optical receiver within the receptacle housing, and an electrical receiver within the receptacle housing. The optical receiver is configured to form the optical connection with the optical terminal when the plug is inserted into the receptacle with the drape therebetween. The electrical receiver is configured to form the electrical connection with the electrical terminal when the plug is inserted into the receptacle with the drape therebetween.

These and other features of the connection system provided herein will become more apparent with reference to the accompanying drawings and the following description, which provide particular embodiments of the connection system in greater detail. For context, a medical device including a portion of a connection system is described first followed by connection systems and methods thereof.

Medical Devices

Figure 1:
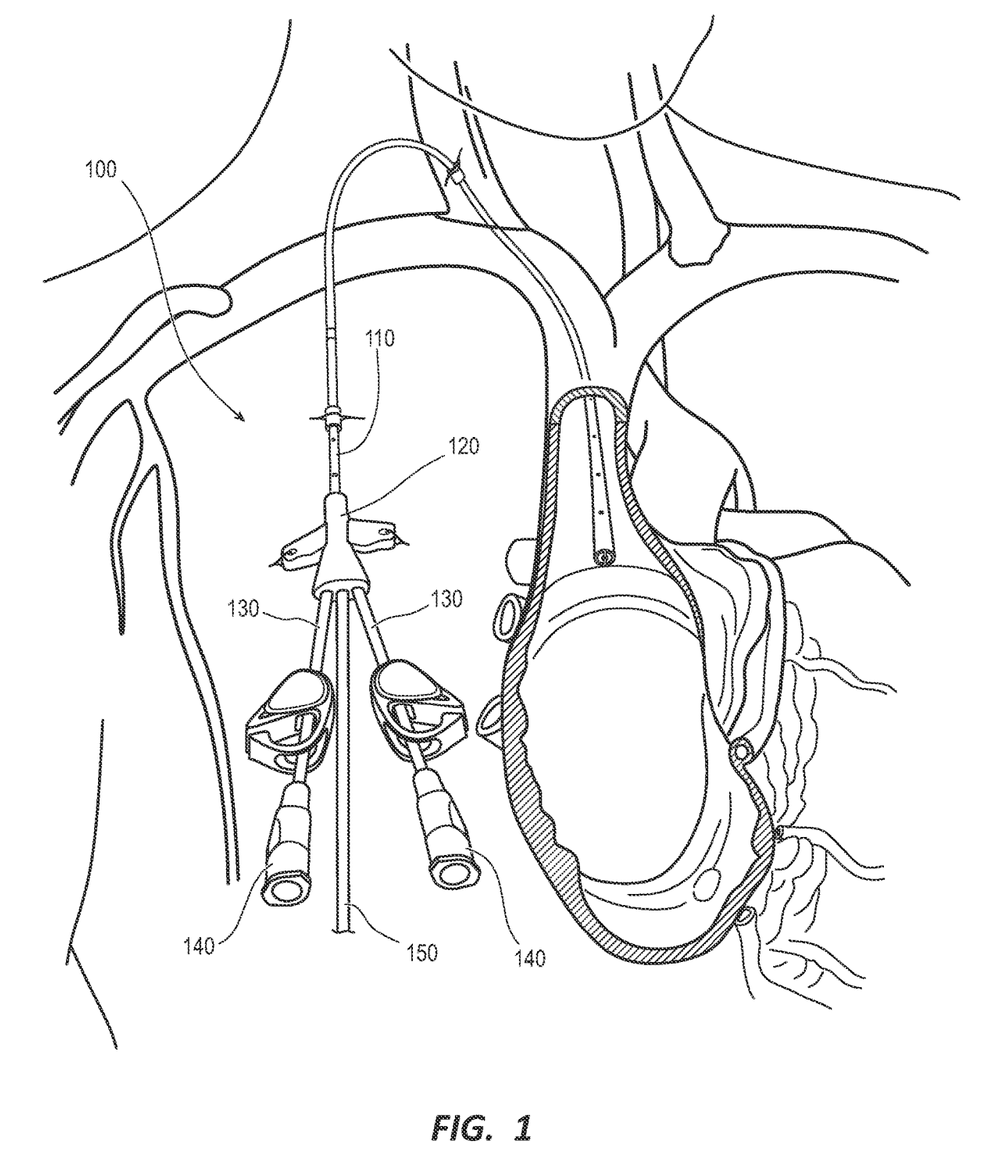
FIG. 1 illustrates a CVC including an integrated optical-fiber stylet in accordance with some embodiments.

FIG. 1 illustrates a CVC 100 including an integrated optical-fiber stylet in accordance with some embodiments.

As shown, the CVC 100 includes a catheter tube 110, a bifurcated hub 120, two extension legs 130, and two Luer connectors 140 operably connected in the foregoing order. While not shown in FIG. 1, the catheter tube 110 includes two catheter-tube lumens and the optical-fiber stylet disposed in a longitudinal bead of the catheter tube 110 such as between the two catheter-tube lumens, as extruded. (See, e.g., optical-fiber stylet 252 in FIG. 2.) In addition, in a same or different longitudinal bead of the catheter tube 110, the CVC 100 can further include an electrocardiogram ("ECG") stylet. The bifurcated hub 120 has two hub lumens correspondingly fluidly connected to the two catheter-tube lumens. Each extension leg of the two extension legs 130 has an extension-leg lumen fluidly connected to a hub lumen of the two hub lumens. The CVC 100 further includes a stylet extension tube 150 extending from the bifurcated hub 120. The stylet extension tube 150 can be a skived portion of the catheter tube 110 including the optical-fiber stylet or the skived portion of the catheter tube 110 disposed in another tube, either of which can terminate in a portion of a connection system such as a connection-system plug as shown in FIG. 2.

While the CVC 100 is provided as a medical device including a portion of a connection system, it should be understood that any of a number of medical devices including catheters such as a PICC can include at least an optical-fiber stylet and a stylet extension tube that terminates in a portion of a connection system for interfacing the optical-fiber stylet with procedural equipment or instrumentation.

Connection Systems

Figure 2:
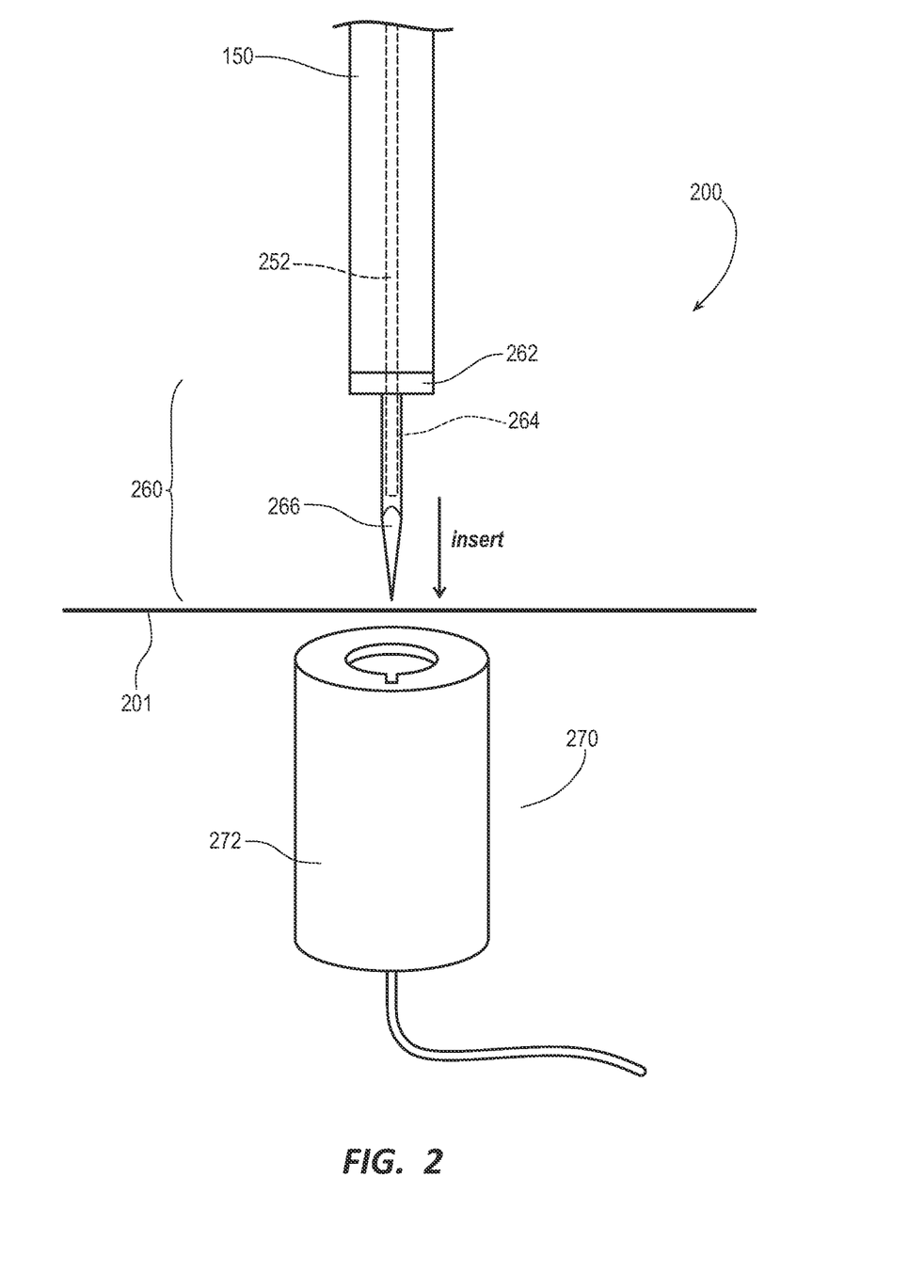
FIG. 2 illustrates a connection system including a plug and a receptacle in accordance with some embodiments.
Figure 3:
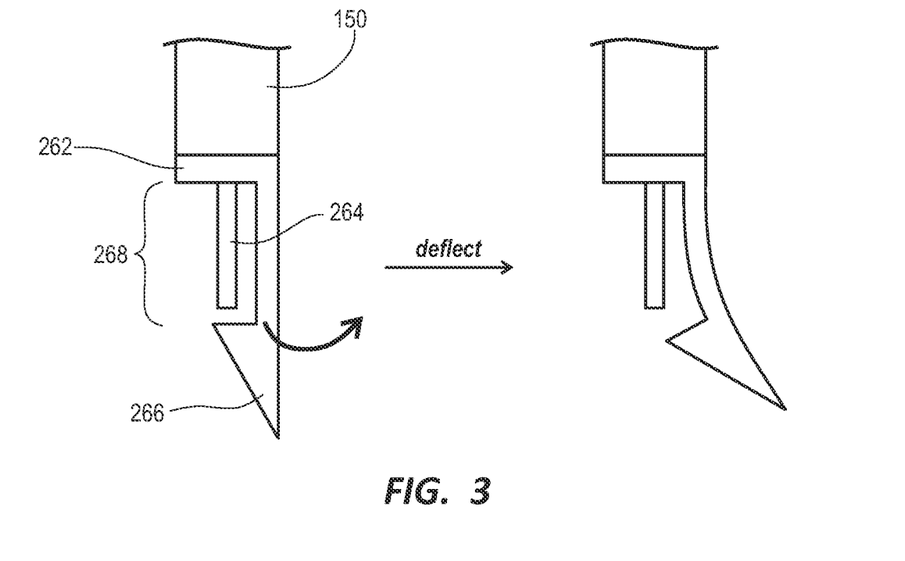
FIG. 3 illustrates deflection of a piercing element of the plug in accordance with some embodiments.
Figure 4:
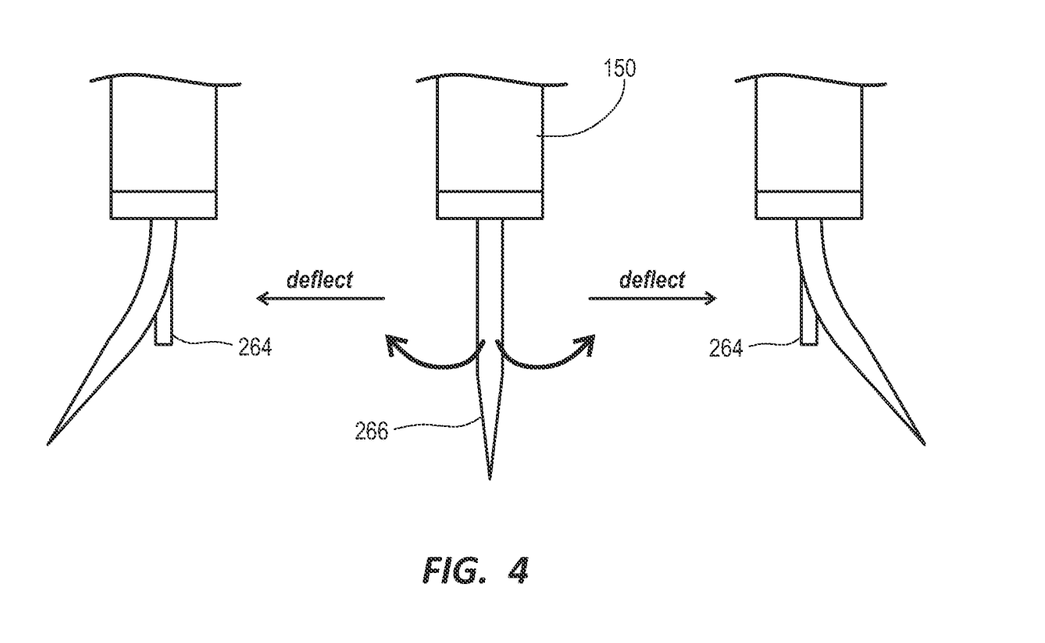
FIG. 4 illustrates deflection of a piercing element of the plug in accordance with some embodiments.

FIG. 2 illustrates a connection system 200 including a plug 260 and a receptacle 270 in accordance with some embodiments. FIGS. 3 and 4 illustrate deflection of a piercing element 266 of the plug 260 in accordance with some embodiments.

As shown in FIG. 2, the connection system 200, which is configured for establishing either an optical connection through a drape 210 or both optical and electrical connections through the drape 201, includes the plug 260 and the receptacle 270. The plug 260 can be at, for example, a proximal-end portion of the stylet extension tube 150 of the CVC 100; however, the plug 260 is not limited to the foregoing medical device as set forth above. From a sterile field established by the drape 201, the plug 260 is configured to insert into the receptacle 270 with the drape 201 therebetween without compromising sterility of the sterile field.

The plug 260 includes a plug housing 262, an optical terminal 264 extending from the plug housing 262, and a piercing element 266 extending from the plug housing 262 for piercing the drape 201. The plug housing 262 can be coupled to, for example, a proximal-end portion of the stylet extension tube 150 of the CVC 100. The piercing element 266 can also be an electrical terminal when the ECG stylet is present, so the electrical terminal is also referenced herein by reference numeral 266. The optical terminal 264 extends from the plug housing 262 into a longitudinal cutout 268 of the piercing element 266 between the plug housing 262 and a tip of the piercing element 266. (See FIG. 3 for the longitudinal cutout 268.) The longitudinal cutout 268 protects the optical terminal 264 from inadvertent damage both before and while piercing the drape 201 with the piercing element 266 to establish the optical connection.

The piercing element 266 is configured to deflect away from a longitudinal axis of the plug 260 to expose the optical terminal 264 as shown in FIG. 3. The piercing element 266 is additionally or alternatively configured to deflect toward one or both longitudinal sides of the plug 260 as shown in FIG. 4.

The receptacle 270, which is generic to other receptacles disclosed herein, includes a receptacle housing 272. Depending upon a particular configuration of the receptacle 270 such as that exemplified by receptacles 570 and 770 respectively of FIGS. 5A-5C and FIGS. 7A and 7B, the receptacle 270 also includes an optical receiver 572 or 772 within the receptacle housing 272 and an electrical receiver 574 or 774 within the receptacle housing 272. (See FIGS.

Figure 7A:
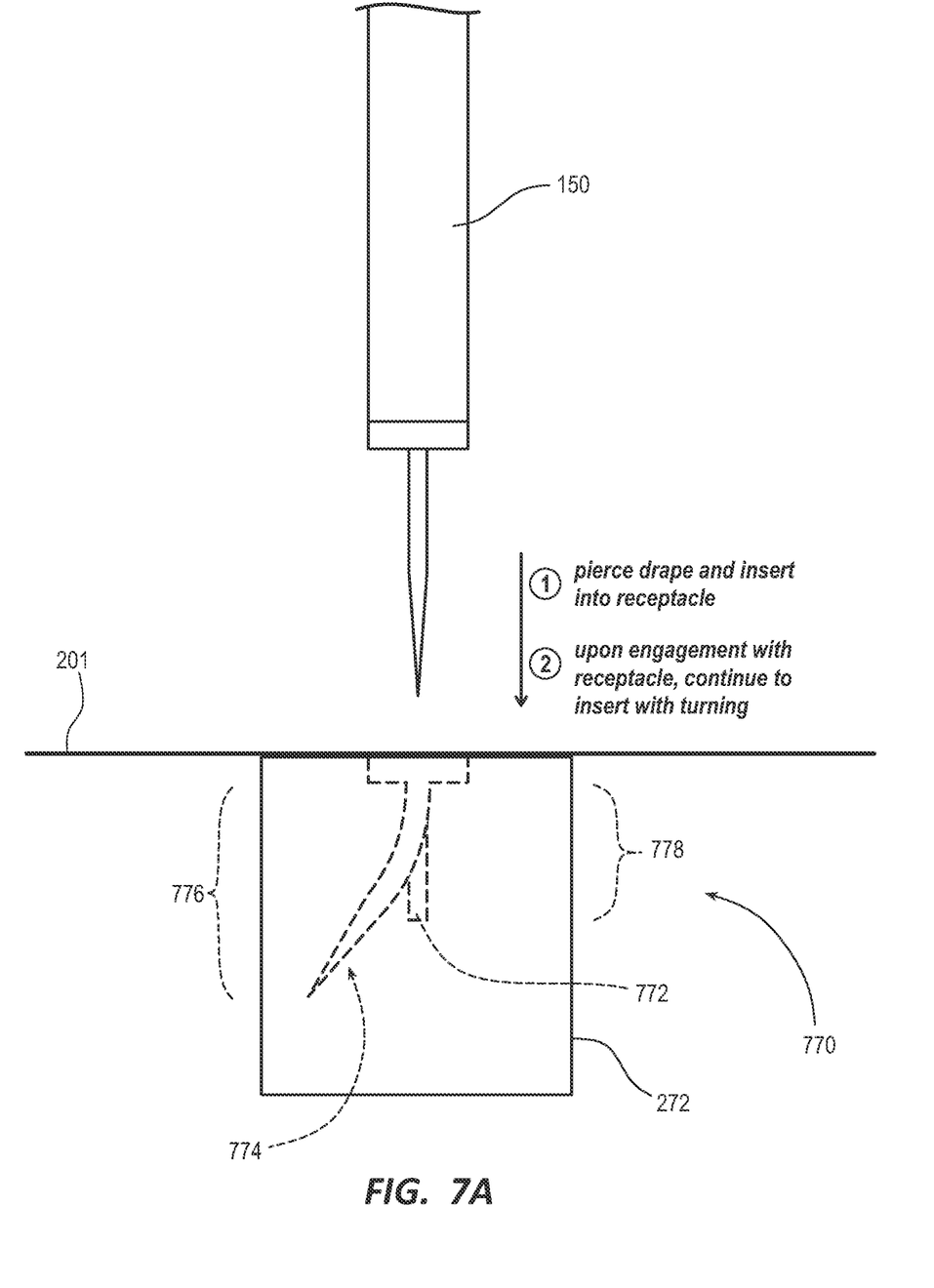
FIG. 7A illustrates insertion of the plug through a drape and into the receptacle in accordance with some embodiments.
Figure 7B:
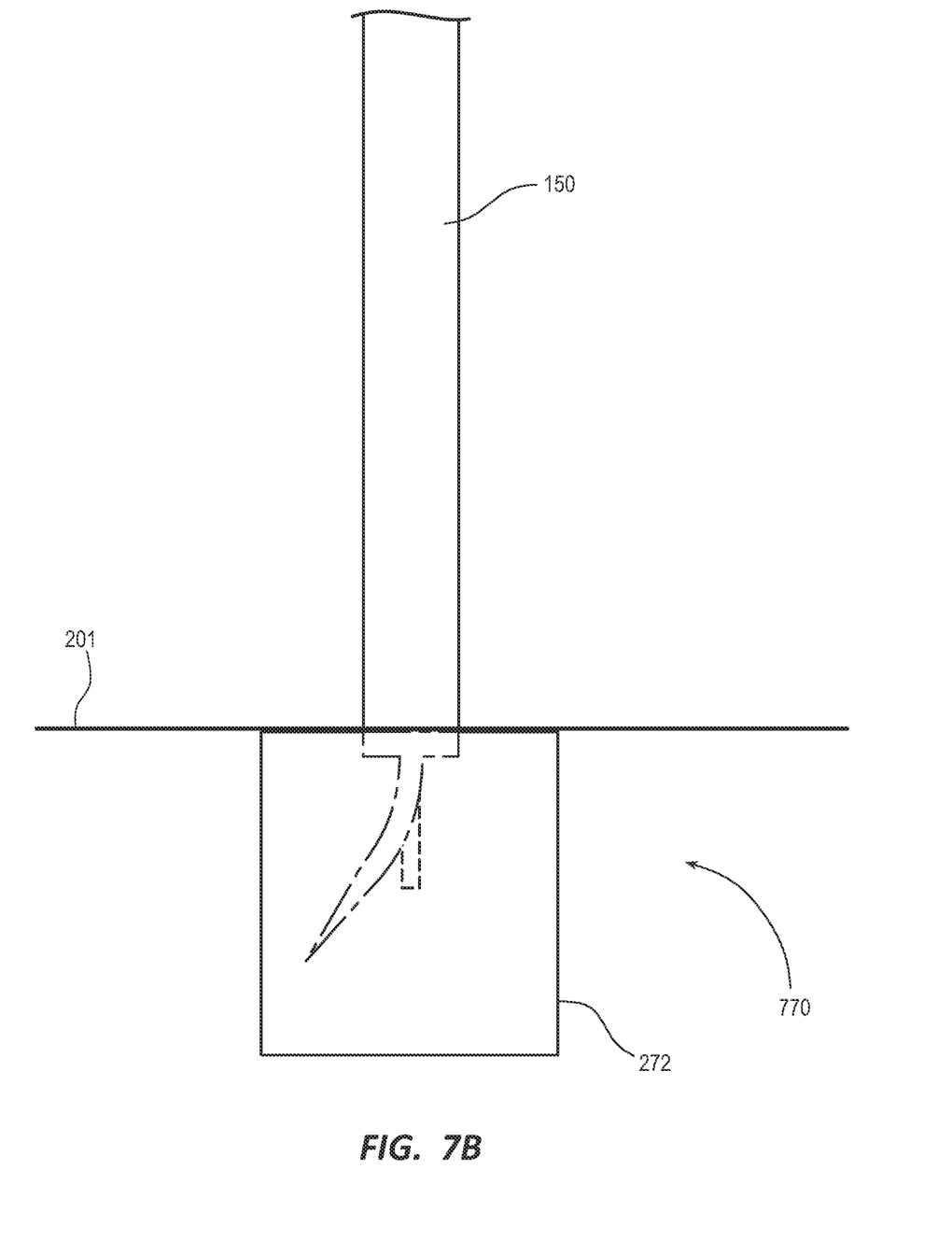
FIG. 7B illustrates complete insertion of the plug through the drape and into the receptacle in accordance with some embodiments.

5A-5C for the optical receiver 572 and electrical receiver 574, and see FIGS. 7A and 7B for optical receiver 772 and electrical receiver 774.) The optical receiver 572 or 772 is configured to form the optical connection with the optical terminal 264 when the plug 260 is inserted into the receptacle 570 or 770 with the drape 201 therebetween. The electrical receiver 574 or 774 is configured to form the electrical connection with the electrical terminal 266 when the plug 260 is inserted into the receptacle 570 or 770 with the drape 201 therebetween.

Figure 5A:
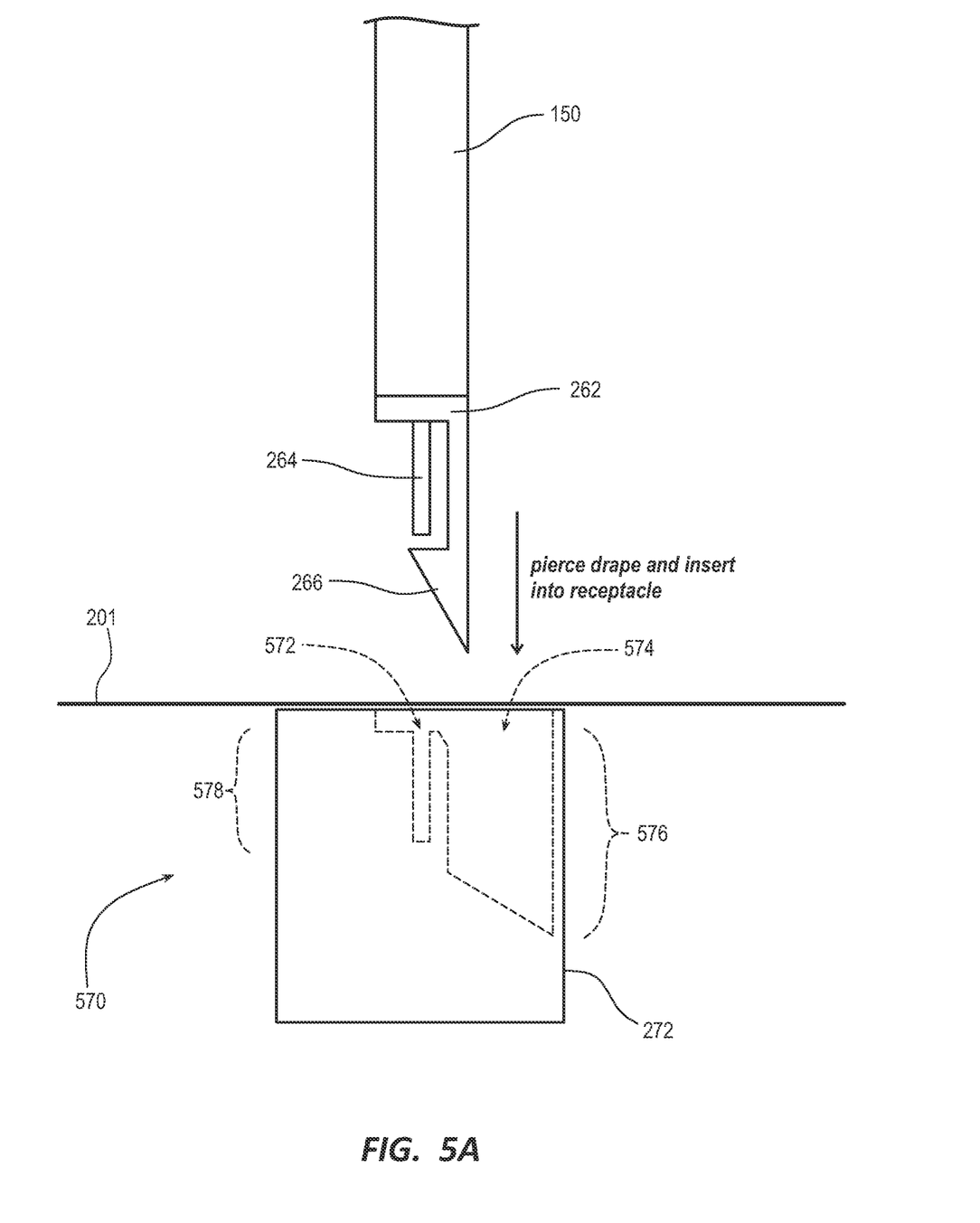
FIG. 5A illustrates insertion of the plug through a drape and into the receptacle in accordance with some embodiments.
Figure 5B:
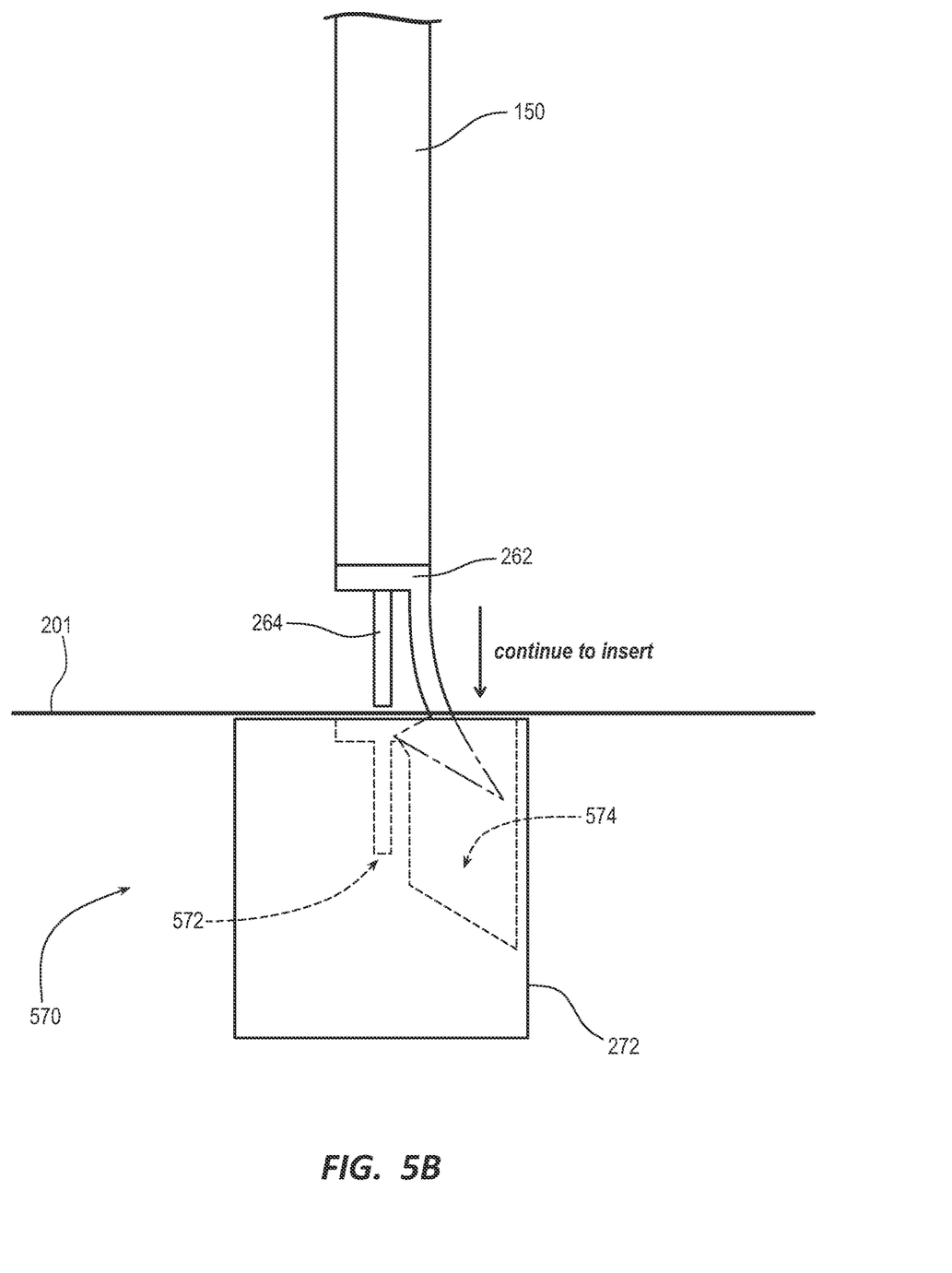
FIG. 5B illustrates continued insertion of the plug through the drape and into the receptacle in accordance with some embodiments.
Figure 5C:
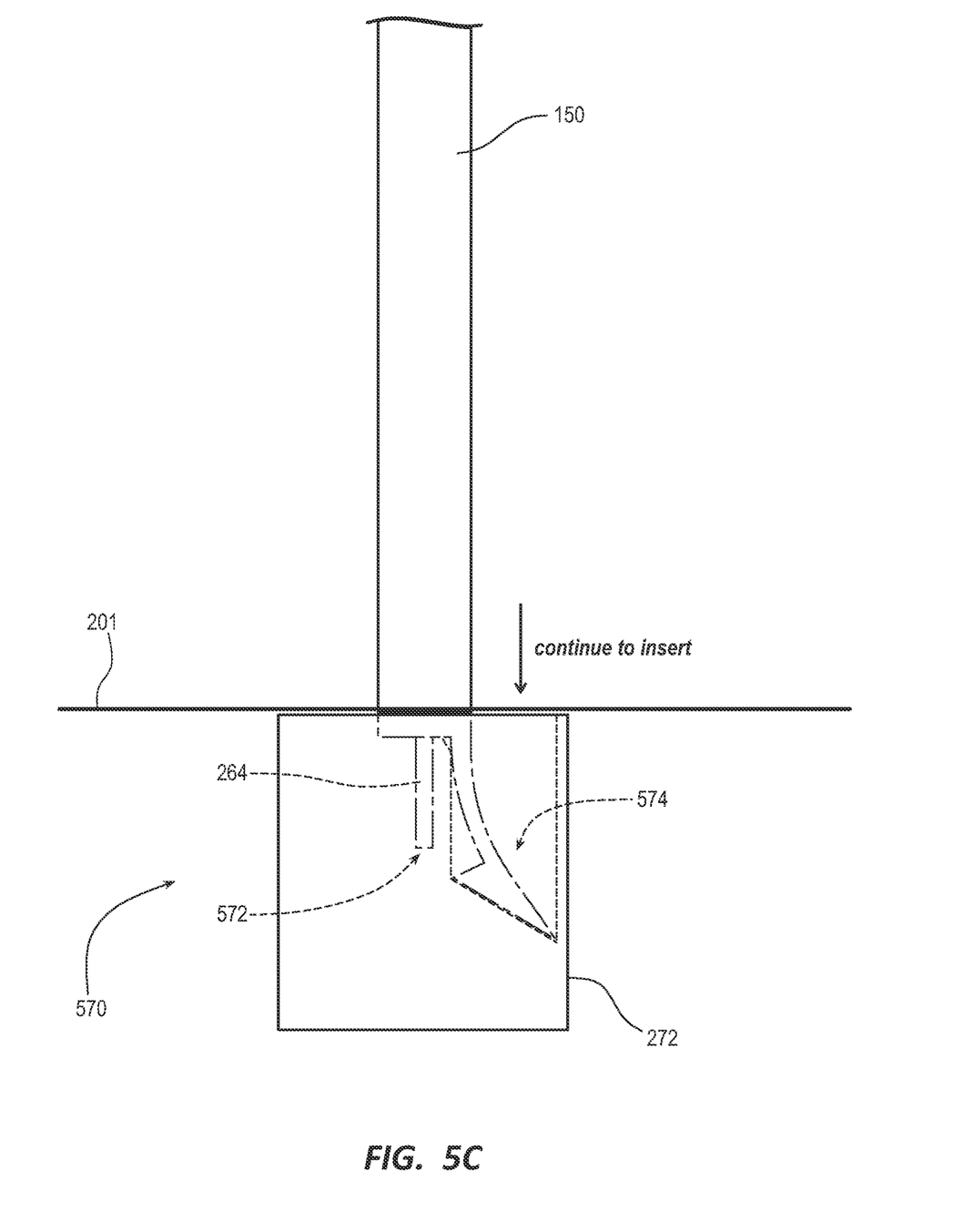
FIG. 5C illustrates complete insertion of the plug through the drape and into the receptacle in accordance with some embodiments.
Figure 6:
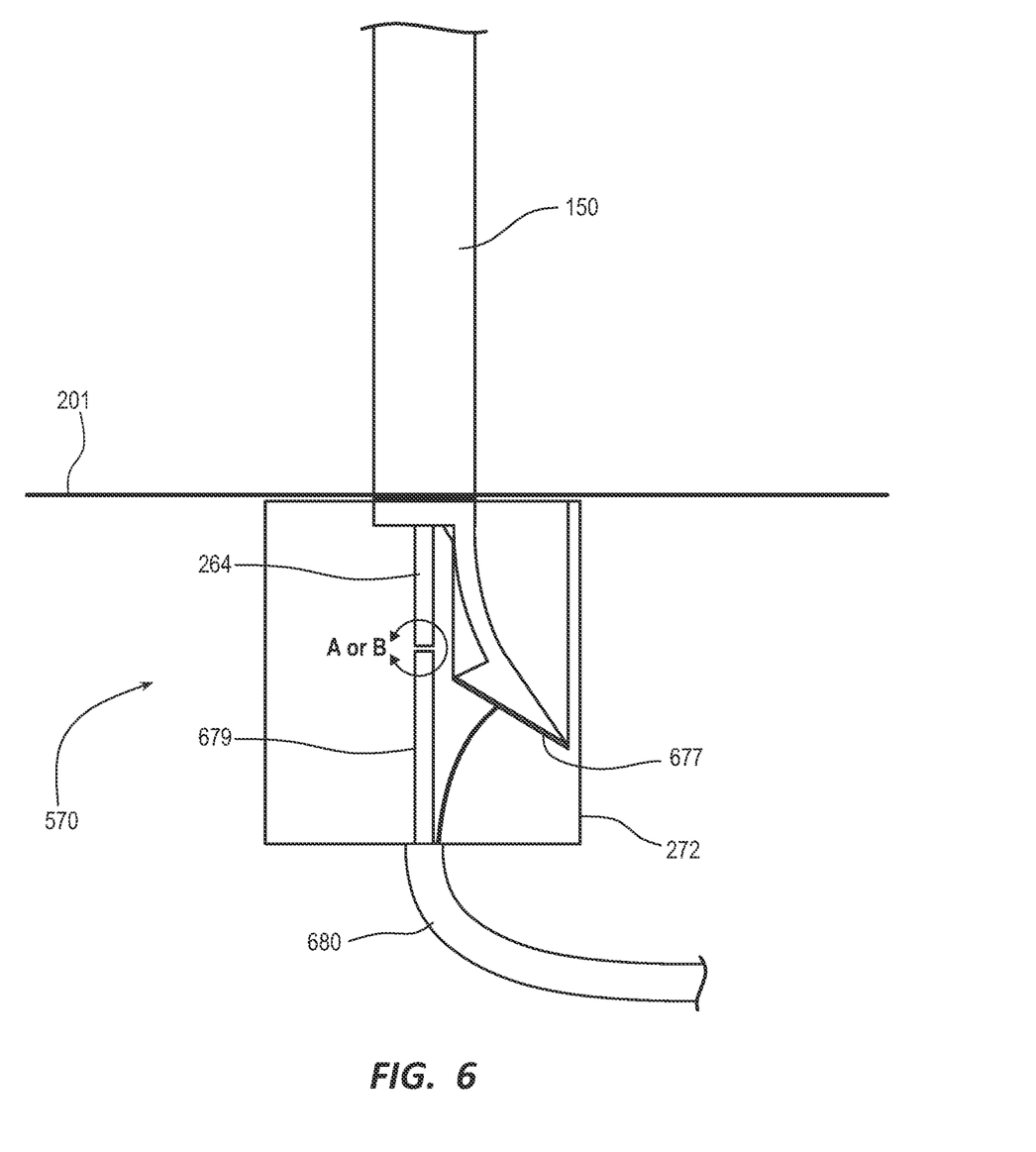
FIG. 6 illustrates a cross-section of the plug completely inserted into the receptacle forming both optical electrical connections in accordance with some embodiments.

FIGS. 5A-5C illustrate insertion of the plug 260 through the drape 201 and into the receptacle 570 in accordance with some embodiments. FIG. 6 illustrates a cross-section of the plug 260 completely inserted into the receptacle 570 forming both optical electrical connections in accordance with some embodiments.

As shown, the receptacle 570 includes the optical receiver 572 and the electrical receiver 574 within the receptacle housing 272. The electrical receiver 574 includes an electrical-receiver channel 576 configured to deflect the piercing element 266 away from the longitudinal axis of the plug 260 upon inserting the plug 260 into the receptacle 570. Deflecting the piercing element 266 away from the longitudinal axis of the plug 260 exposes the optical terminal 264 for insertion into an optical-receiver channel 578 of the optical receiver 572 and formation of the optical connection. The electrical-receiver channel 576 is further configured to keep the piercing element 266 deflected away from the longitudinal axis of the plug 260 to maintain the optical connection. The electrical-receiver channel 576 is even further configured to form the electrical connection with an electrical contact 677 within the electrical receiver 574 such as at a bottom of the electrical receiver 574 upon fully inserting the plug 260 into the receptacle 570. Likewise, the optical-receiver channel 578 is configured to form the optical connection with an end portion of an optical fiber 679 within the optical receiver 572 such as at a bottom of the optical receiver 572 upon fully inserting the plug 260 into the receptacle 570. The electrical contact 677 is electrically connected (e.g., soldered) to a wire, and both the optical fiber 679 and the wire extend from the receptacle 570 in a same or different cable 680 as shown.

FIGS. 7A and 7B illustrates insertion of the plug 260 through the drape 201 and into a receptacle 770 in accordance with some embodiments. Note, the plug 260 of FIGS. 7A and 7B is that of FIGS. 5A-5C but rotated clockwise around the longitudinal axis of the stylet extension tube 150 about 90°.

As shown, the receptacle 770 includes the optical receiver 772 and the electrical receiver 774 within the receptacle housing 272. The electrical receiver 774 includes an electrical-receiver channel 776 configured to deflect the piercing element 266 toward the longitudinal side of the plug 260 upon inserting the plug 260 into the receptacle 770 and turning the plug 260 upon engagement with the receptacle 770, for example, about a ¼ turn. Deflecting the piercing element 266 toward the longitudinal side of the plug 260 exposes the optical terminal 264 for insertion into an optical-receiver channel 778 of the optical receiver 772 and formation of the optical connection. The electrical-receiver channel 776 is further configured to keep the piercing element 266 deflected toward the longitudinal side of the plug 260 to maintain the optical connection. The electrical-receiver channel 776 is even further configured to form the electrical connection with an electrical contact within the electrical receiver 774 such as at a bottom of the electrical receiver 774 upon fully inserting the plug 260 into the receptacle 770. (For an example electrical contact, see the electrical contact 677 of FIG. 6.) Likewise, the optical-receiver channel 778 is configured to form the optical connection with an end portion of an optical fiber within the optical receiver 772 such as at a bottom of the optical receiver 772 upon fully inserting the plug 260 into the receptacle 770. (For an example optical connection, see the optical connection between the optical terminal 264 and the end portion of the optical fiber 679 in FIG. 6.)

Figure 8A:
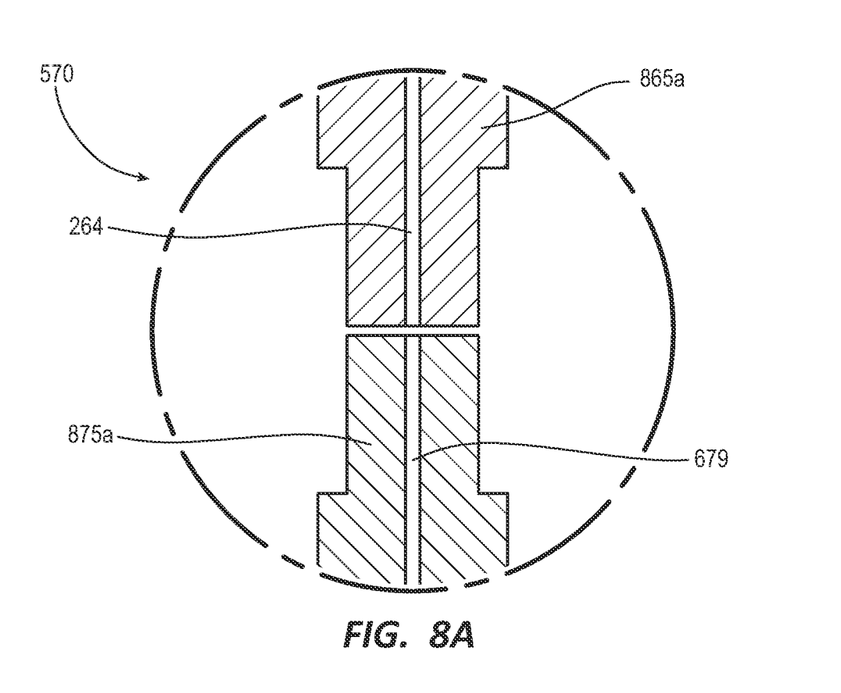
FIG. 8A illustrates a straight sleeve-type butt-joint connection of an optical connection in accordance with some embodiments.
Figure 8B:
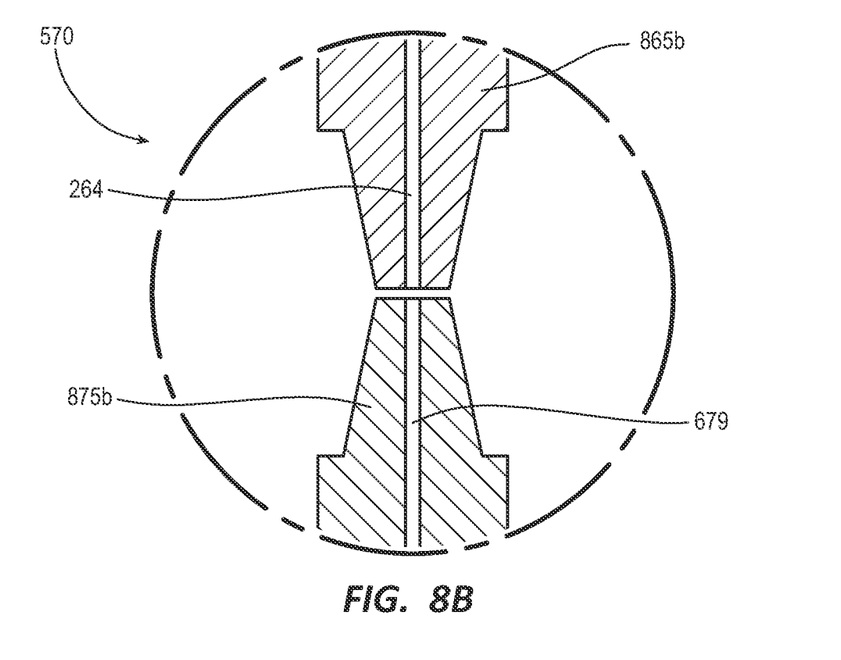
FIG. 8B illustrates a tapered sleeve-type butt-joint connection of an optical connection in accordance with some embodiments.

FIG. 8A illustrates a straight sleeve-type butt-joint connection of an optical connection in accordance with some embodiments. FIG. 8B illustrates a tapered sleeve-type butt-joint connection of an optical connection in accordance with some embodiments.

As shown among FIGS. 5A, 7, 8A and 8B, the optical terminal 264, which is a proximal-end portion of an optical fiber such as that of the optical-fiber stylet 252, extends from the plug housing 262 into a ferrule 865a or 865b. The optical receiver 572 includes the optical fiber 679 disposed in a ferrule 875a or 875b at a closed end or bottom of the optical receiver 572. Likewise, the optical receiver 772 can include the optical fiber 679 disposed in the ferrule 875a or 875b at a closed end or bottom of the optical receiver 772. The ferrules 865a and 875a connect in a straight sleeve-type butt-joint connection for the optical connection. The ferrules 865b and 875b connect in a tapered sleeve-type butt-joint connection for the optical connection.

Methods

A method for establishing both an optical connection and an electrical connection through the drape 201 includes establishing a sterile field with the drape 201; piercing the drape 201 from a sterile side thereof with the electrical terminal or piercing element 266 that extends from the plug 260, wherein the piercing element 266 includes the longitudinal cutout 268 between the housing 262 of the plug 260 and a tip of the piercing element 266 in which cutout 268 the optical terminal 264 that extends from the plug 260 is disposed; inserting the plug 260 into the receptacle 570 or 770 on a non-sterile side of the drape 201, wherein the receptacle 570 or 770 includes the optical receiver 572 or 772 and the electrical receiver 574 or 774 within the receptacle housing 272 configured to form the optical connection with the optical terminal 264 and the electrical connection with the piercing element 266, respectively; and establishing both the optical and electrical connections through the drape 201 without compromising sterility of the sterile field.

Piercing the drape 201 with the piercing element 266 simultaneously advances the optical terminal 264 through the drape 201 in accordance with disposition of the optical terminal 264 in the longitudinal cutout 268 of the piercing element 266.

Inserting the plug 260 into the receptacle 570 or 770 includes inserting the piercing element 266 into the electrical-receiver channel 576 or 776. The electrical-receiver channel 576 or 776 is configured to deflect the piercing element 266 away from the longitudinal axis of the plug 260 or toward the longitudinal side of the plug 260. Deflecting the piercing element 266 away from the longitudinal axis of the plug 260 or toward the longitudinal side of the plug 260 exposes the optical terminal 264.

Inserting the plug 260 into the receptacle 570 or 770 includes forming a butt-joint connection between a ferrule-covered portion of the optical terminal 264 and a ferrule-covered portion of the optical fiber 679 at a closed end of the optical receiver 572 or 772.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A method for establishing both an optical connection and an electrical connection through a drape, comprising:
    piercing the drape from a sterile side with a piercing tip of an electrical terminal extending from a plug housing of a plug, the plug further comprising an optical terminal extending from the plug housing;
    inserting the plug into a receptacle, the receptacle comprising a receptacle housing, an electrical receiver, and an optical receiver;
    establishing the electrical connection between the electrical receiver and the electrical terminal; and
    establishing the optical connection between the optical terminal and the optical receiver.

2. The method according to claim 1, wherein the electrical terminal includes a longitudinal cutout between the plug housing and the piercing tip, and wherein the optical terminal extends into the longitudinal cutout, the method further comprising deflecting the electrical terminal away from the optical terminal when establishing the electrical connection and the optical connection.

3. The method according to claim 2, further comprising inserting the electrical terminal into an electrical receiver channel, and inserting the optical terminal into an optical receiver channel separate from the electrical receiver channel after deflecting the electrical terminal away from the optical terminal.

4. The method according to claim 3, wherein the electrical receiver channel includes an angled bottom surface having a length to match a length of a side of the electrical terminal, and wherein inserting the electrical terminal into the electrical receiver channel comprises contacting the angled bottom surface with the side of the electrical terminal.

5. The method according to claim 1, further comprising deflecting the electrical terminal away from the optical terminal when establishing the electrical connection and the optical connection.

6. The method according to claim 5, further comprising inserting the electrical terminal into an electrical receiver channel, and inserting the optical terminal into an optical receiver channel separate from the electrical receiver channel after deflecting the electrical terminal away from the optical terminal.

7. The method according to claim 6, wherein the electrical receiver channel has a shape corresponding to the shape of the electrical terminal, and wherein the optical receiver channel has a shape corresponding to the shape of the optical terminal.

8. The method according to claim 1, wherein the optical terminal includes a first optical fiber extending into a first ferrule, wherein the optical receiver includes a second optical fiber disposed in a second ferrule, and wherein establishing the optical connection between the optical terminal and the optical receiver comprises connecting the first ferrule and the second ferrule in a straight sleeve-type butt-joint connection.

9. The method according to claim 1, wherein the optical terminal includes a first optical fiber extending into a first ferrule, wherein the optical receiver includes a second optical fiber disposed in a second ferrule, and wherein establishing the optical connection between the optical terminal and the optical receiver comprises connecting the first ferrule and the second ferrule in a tapered sleeve-type butt-joint connection.

* * * * *